United States Patent [19]
Kan

[11] Patent Number: 5,906,574
[45] Date of Patent: May 25, 1999

[54] APPARATUS FOR VACUUM-ASSISTED HANDLING AND LOADING OF RADIOACTIVE SEEDS AND SPACERS INTO IMPLANT NEEDLES WITHIN AN ENCLOSED VISIBLE RADIATION SHIELD FOR USE IN THERAPEUTIC RADIOACTIVE SEED IMPLANTATION

[76] Inventor: William C. Kan, 2000 Duker Trace, Dothan, Ala. 36303

[21] Appl. No.: 08/933,826

[22] Filed: Sep. 19, 1997

Related U.S. Application Data

[63] Continuation-in-part of application No. 08/540,540, Oct. 6, 1995, abandoned.
[51] Int. Cl.$^6$ ................................................. A61M 36/00
[52] U.S. Cl. ...................... 600/7; 600/5; 600/3; 221/211; 414/146
[58] Field of Search .................................. 600/1, 3, 4, 5, 600/7; 221/211; 414/146

[56] References Cited

U.S. PATENT DOCUMENTS

| | | | |
|---|---|---|---|
| 4,364,376 | 12/1982 | Bigham | 600/5 |
| 5,120,973 | 6/1992 | Rohe et al. | 600/3 |
| 5,147,282 | 9/1992 | Kan . | |
| 5,342,283 | 8/1994 | Good | 600/8 |
| 5,562,232 | 10/1996 | Pearson | 221/211 |
| 5,716,317 | 2/1998 | Okano et al. | 600/5 |

Primary Examiner—Lee Cohen
Assistant Examiner—Rosiland Kearney
Attorney, Agent, or Firm—Jacobson, Price, Holman & Stern, PLLC

[57] ABSTRACT

A vacuum assisted handling and loading of radioactive seeds into implant needles from a lead glass shielded glass tube and with seeds manipulated within an enclosed visible radiation shield. Radioactive seeds and spacers are located on a loading platform within a shield having at least two transparent side walls for viewing into the interior of the shield. A vacuum pickup probe is inserted into the shield to manipulate the radioactive seeds and spacers to lift and drop the radioactive seeds and spacers into the funnel leading to a glass tube, behind a lead glass window. The manipulation of the vacuum pickup probe is performed from outside of the shield and vacuum force exerted through the pickup probe and the glass tube on the radioactive seeds or spacers. When the desired sequence of seeds and spacers has been achieved and visually verified through the glass tube window, the implant needle within its slip shield body is positioned through the visible radiation shield to dock with the funnel opening of the glass tube in the loading platform. A vacuum force is applied to the interior of the implant needle and the sequence of seeds/spacers in the glass tube is drawn up into the docked implant needle surrounded by a slip shield body. While the needle interior vacuum is still active, the loaded implant needle in the slip shield body is withdrawn from the visible radiation shield docking position and the terminal end of the implant needle is sealed and placed in a needle slip shield holder according to a template designation.

24 Claims, 15 Drawing Sheets

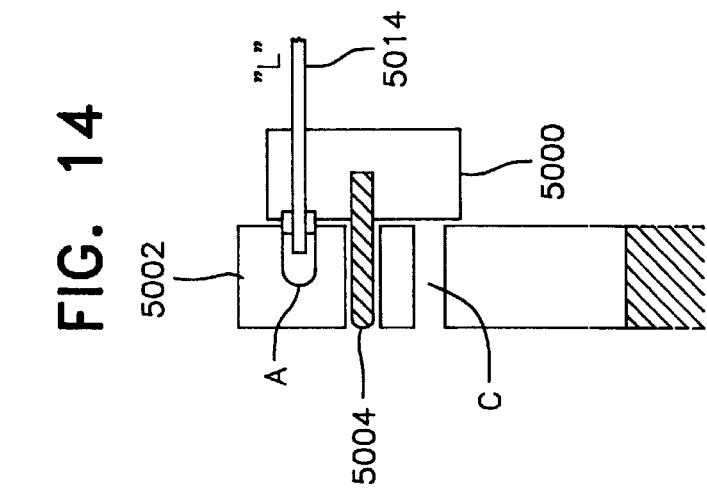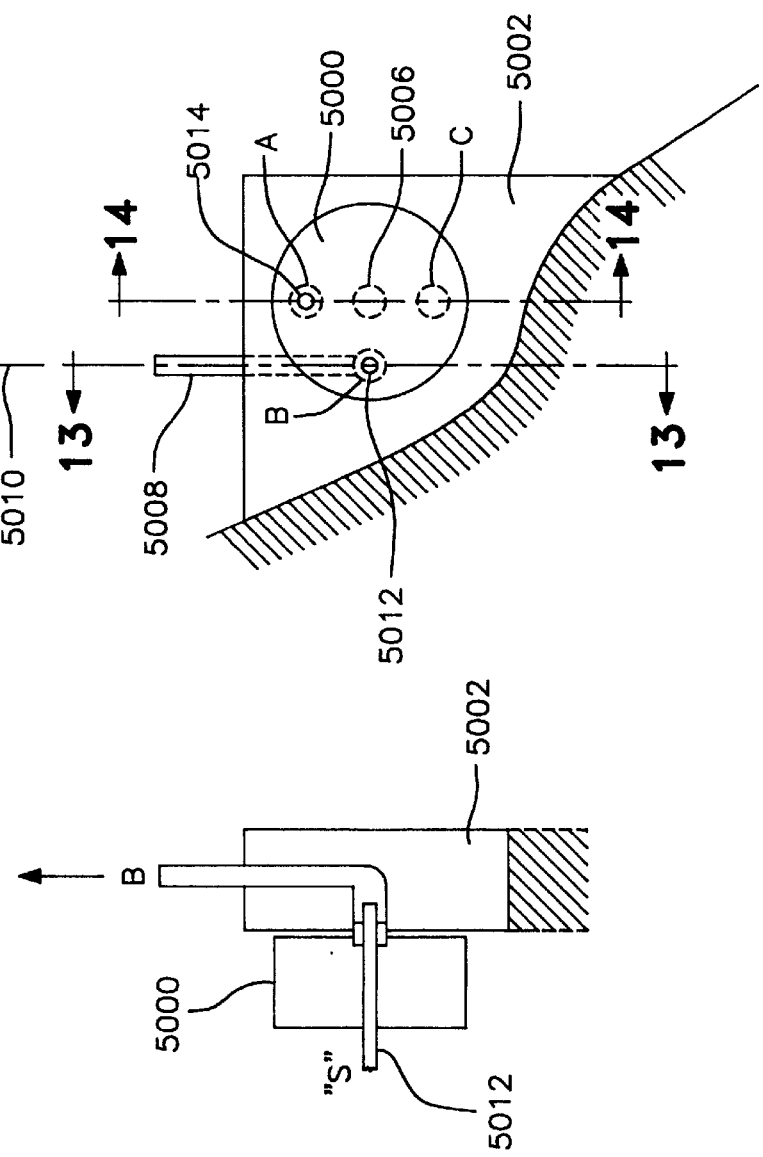

APPARATUS FOR VACUUM-ASSISTED HANDLING AND LOADING OF RADIOACTIVE SEEDS AND SPACERS INTO IMPLANT NEEDLES WITHIN AN ENCLOSED VISIBLE RADIATION SHIELD FOR USE IN THERAPEUTIC RADIOACTIVE SEED IMPLANTATION

This application is a continuation-in-part of application Ser. No. 08/540,540, filed Oct. 6, 1995, now abandoned the subject matter of which is herein incorporated in its entirety by reference.

FIELD OF THE INVENTION

The present invention simplifies the handling and loading of radioactive seeds, permits visual verification of the needle contents immediately prior to needle loading and eliminates radiation exposure to personnel during the loading of radioactive seeds into implant needles and in the handling of seed-bearing needles.

BACKGROUND OF THE INVENTION

Prior practices involving the use of radioactive seeds for medical treatment have involved the use of unsafe methods for movement of radioactive seeds from storage and for loading of radioactive seeds using forceps and exposing the hands of individuals to radiation. These prior practices do not provide a safe, reliable and accurate means of handling and loading radioactive seeds into implant needles nor do they allow a verification of the loaded contents.

Accordingly, it is desired to provide a safe and accurate method and apparatus for handling and loading radioactive seeds into implant needles and at the same time provide a means of verifying the number and arrangement of radioactive seeds and spacers that are in the implant needle.

SUMMARY OF THE INVENTION

Accordingly, an apparatus is provided according to the principles of the present invention for vacuum assisted handling and loading of radioactive seeds into implant needles within an enclosed, visible radiation shield.

This object is achieved by the use of an implant needle located within a needle slip shield body. The implant needle and slip shield body are inverted and fixed in position within an acceptance funnel of a loading platform containing radioactive seeds and spacers.

A vacuum force is applied to the interior of the implant needle. A terminal end of the implant needle is located within an acceptance funnel opening up into a surface of the loading platform having radioactive seeds and spacers. The radioactive seeds and spacers located on the loading platform are located within a shield having at least two transparent side walls for viewing into the interior of the shield.

A vacuum pickup probe is inserted into the shield to manipulate the radioactive seeds and spacers to lift and drop the radioactive seeds and spacers into the funnel leading to the terminal end of the implant needle. The manipulation of the vacuum pickup probe is performed from outside of the shield and the vacuum force exerted on the radioactive seeds or spacers is controlled exteriorly of the shield.

A predetermined sequence and number of radioactive seeds and spacers are fed into the inverted implant needle. When the desired sequence has been achieved, the end of the slip shield body adjacent to the terminal end of the implant needle is sealed in an upright position and the implant needle is inverted again, back to a normal use position. The vacuum force in the implant needle is then removed. The sequence of radioactive seeds and spacers is thereby maintained in the implant needle in a desired positioning.

Assembled implant needles positioned within a protective needle slip shield body are positionable in a needle holder box having a plurality of opening for holding a desired order of assembled implant needles having predetermined sequences of seeds and spacers. The assembled implant needles have assigned locations for ease of retrieval and identification. The assembled needles are thereby maintained in a locateable position until needed for use.

In an alternate embodiment of the present invention, an apparatus is provided according to the principles of the present invention for vacuum assisted handling and controlling of radioactive seeds and spacers from outside of a domed enclosure to form a seed/spacer column. The domed enclosure is formed by a radiation shield through which the seeds and spacers are visible. For loading seeds into implant needles, each empty needle is fitted with its own radiation shield, called the slip shield, and with the implant needle tip exposed, are introduced from outside the domed enclosure to the interior for pick up of the formed seed/spacer column by vacuum introduced from the hub end of the needle.

This objective is achieved by inserting a vacuum pickup probe through a top opening of the domed enclosure shield to manipulate the radioactive seeds and spacers on the loading platform to lift and drop the radioactive seeds and spacers into a funnel leading into a glass tube. The lower end of the glass tube is connected to a vacuum which is activated together with the vacuum of the pickup probe. The glass tube is located behind a lead glass window for visual verification of a proper arrangement of seeds and spacers in a column prior to needle transfer.

The glass tube is constructed extending downwardly from the loading platform. The glass tube having radioactive seeds and spacers forms a lower extension of the loading platform of the domed enclosure. The diameters of commercially available I-125 or Pd-103 seeds as well as spacers are such that they easily fit within the inner diameter of both the glass tube and an 18 gauge implant needle. Spacers are made of cat gut suture material.

A second objective is achieved by applying a vacuum force from the needle hub to the interior of an empty implant needle with the needle tip being exposed when the slip shield end cap is removed. With the vacuum source activated and the tip exposed, the shielded empty needle is lowered into the domed enclosure from the top opening onto the loading platform to pick up an arrangement of seeds and spacers from a column inside the glass tube. The particular seed/spacer column arrangement is specific for a template matrix patient location.

A predetermined sequence and number of radioactive seeds and spacers are fed into the shielded window glass tube forming a seed/spacer column. When the desired sequence has been visibly verified in the glass tube, the seed/spacer column is ready for transfer to an implant needle. An implant needle within a slip shield body with needle tip protruding, docks with the funneled opening in the loading platform leading to the glass tubes. A vacuum force is applied to the interior of the implant needle and the column of radioactive seeds and spacers in the glass tube is now drawn up by the vacuum into the implant needle within the slip shield body.

The implant needle and slip shield body are removed from the visible radiation shield and the terminal end of the implant needle protruding from the slip shield is sealed with bone wax. The vacuum force in the implant needle is then removed, replaced with a stylet and fixed in position to hold the seed/spacer column in place. After the stylet displacement due to radioactive seeds and spacers has been visually verified, a locking collar is used to look the stylet in place on the needle, thereby protecting the seed/spacer column inside the tip end of the implant needle.

It is another object of the present invention to provide an implant needle which is positionable within a needle slip shield body and securable in an upright position above a loading platform of a shielded assembly area with a visible window glass tube containing a predetermined and visually verified sequence column of radioactive seeds/spacers for transfer to an implant needle by means of a vacuum receiving probe.

Assembled implant needles positioned within a protective needle slip shield body are positionable in a needle holder box having a plurality of openings for holding a desired order of assembled implant needles having predetermined and verified sequences of seeds and spacers. The assembled implant needles have assigned locations for ease of retrieval and identification. The assembled needles are thereby maintained in a locateable position until needed for use.

It is still yet another object of the present invention to provide an implant needle which is positionable within a needle slip shield body and securable in an upright position above a loading platform of a shielded assembly area with a visible window glass tube containing a predetermined and visually verified sequence of radioactive seeds and spacers for positioning in the implant needle by a vacuum receiving probe within the shielded assembly area made of lead glass plates.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 12 is a view of a portion of a platform stand having a switch for controlling the direction of evacuation of air to a vacuum source.

FIG. 13 is a sectional view taken along line 13—13 of FIG. 12.

FIG. 14 is a sectional view taken along line 14—14 of FIG. 12.

DETAILED DESCRIPTION OF THE PREFERRED EMBODIMENTS

Figure 1:
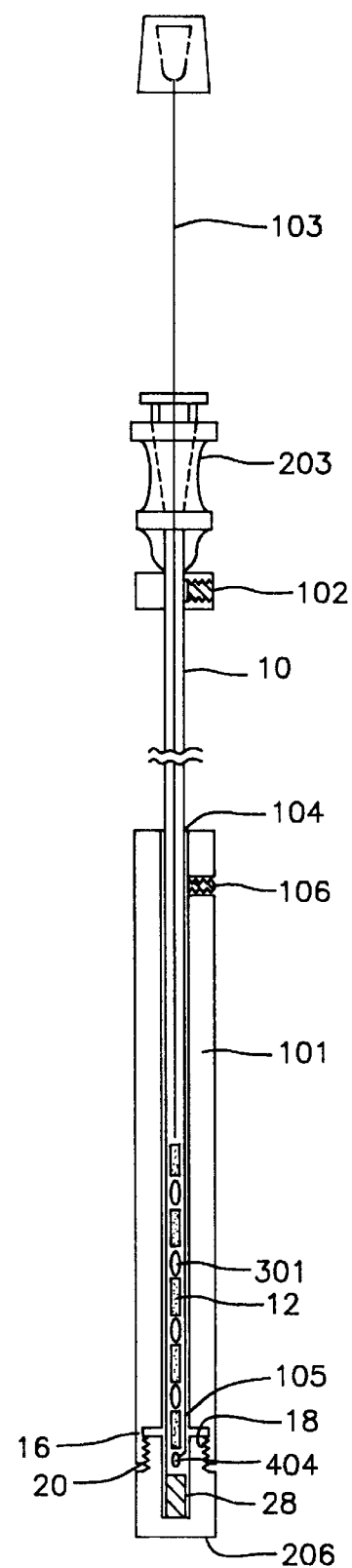
FIG. 1 is a partial sectional view of an assembled implant needle located within a needle slip shield body with a capped end and a sequence of radioactive seeds and spacers located at a distal end of the implant needle.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

1) Placement of radiation slip shield body 101 on individual needles prior to seed loading.

A needle locking collar 102 is placed onto an empty implant needle 10 and the needle 10, without the stylet 103, is inserted into the opening 104 of a protective needle slip shield body 101 with the needle tip 105 pointing down, as shown in FIG. 1, and extending to the end 16 of body 101. End 16 includes internal threads 18. By tightening the radially extending lock screw 106 of the needle slip shield body 101 which passes through the body 101 and contacts the needle 10, the relative position between the needle 10 and shield body 101 is fixed.

Although the needle slip shield body 101 can be constructed more economically from a single material such as stainless steel, for more efficient radiation shielding, lead or other higher atomic number materials can also be used. Also, two concentric tubes may be used with lead fill material between the two tubes. This construction principle is demonstrated in U.S. Pat. No. 5,147,282.

2) Creation of a vacuum in the needle using a vacuum extension probe, allowing seed loading from the needle tip into the needle.

Figure 2:
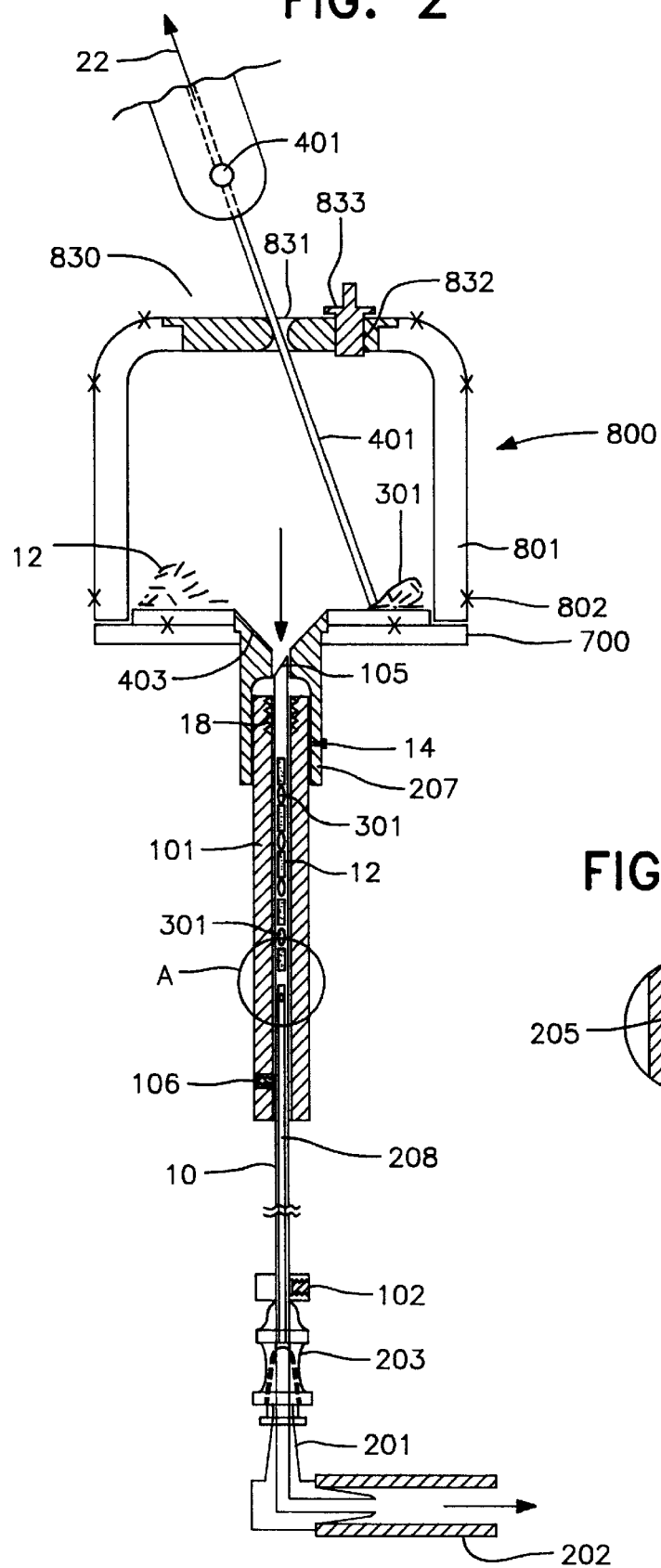
FIG. 2 is a sectional view of an apparatus for placing a sequence of radioactive seeds and spacers in a distal end of an implant needle which is secured in an inverted position under a loading platform of a shielded area.
Figure 2A:
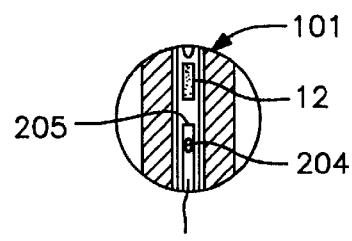
FIG. 2A is an enlarged view of the area encircled by "A" in FIG. 2.

A vacuum extension probe 201, with hose 202 attached to a vacuum pump/vacuum source, is inserted into the implant needle head 203. A tubular portion 208 of the probe 201 is inserted inside of the needle 10. A side opening 204 at the end of the probe tubular portion 208 assures vacuum flow even if the tip end opening 205 is blocked by the nearest seed 12 during seed loading, thereby maintaining vacuum throughout the needle 10, needle tip 105 and funnel 403 during seed loading. With the end cap 206 of the slip shield body 101 removed by unscrewing the internal threads 18 from the external threads 20 of the cap 206, body 101 and the needle tip 105 are exposed. The slip shield with needle 10 is inverted and inserted into the needle receptacle 207 under the loading platform 700 of the mini-dome shield 800 as shown in FIG. 2. A set screw 14 extending radially through the needle receptacle 207 secures the body 101 to the needle receptacle 207. The needle 10 is now ready for seed loading.

3) Introduction of seeds and spacers to the platform for loading.

Figure 3:
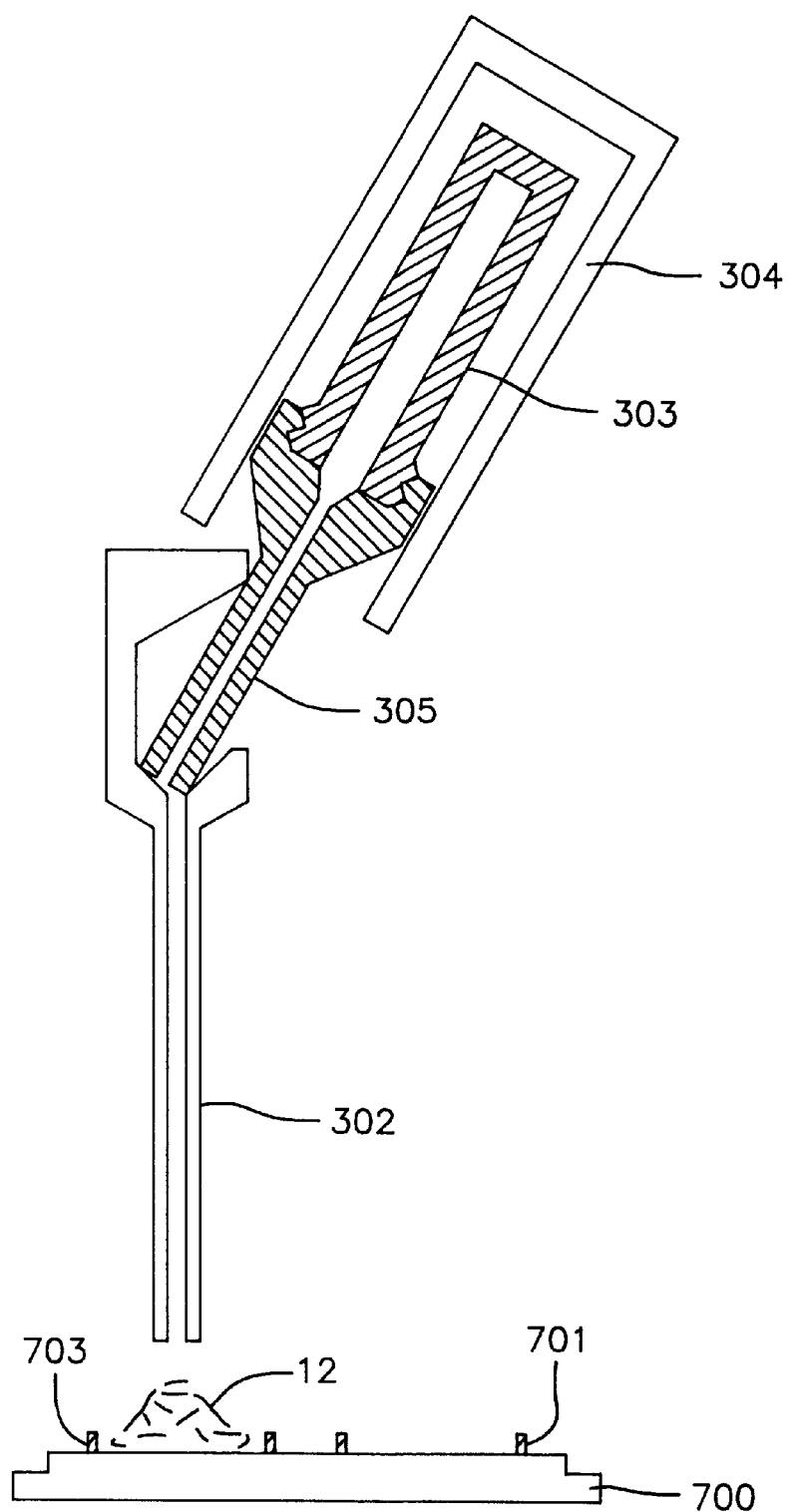
FIG. 3 is a sectional view of a system for placing radioactive seeds and spacers on a loading platform.
Figure 3A:
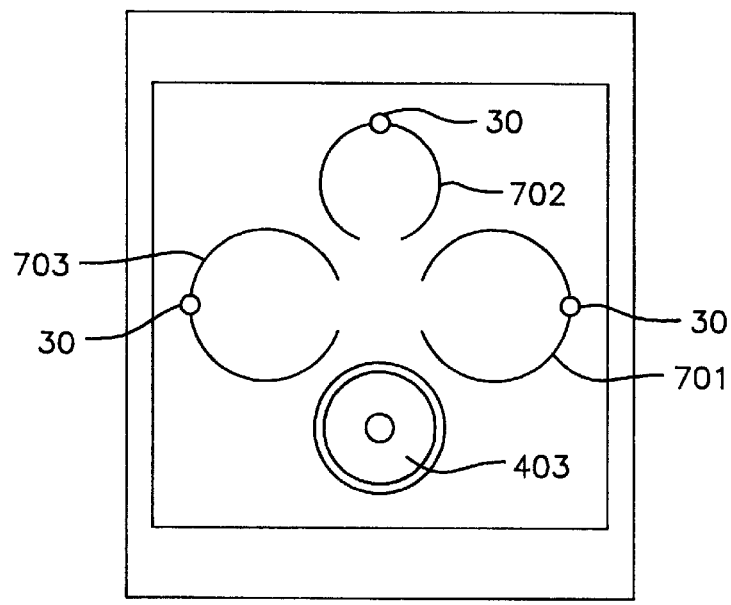
FIG. 3A is a plan view of the loading platform.

A loading platform 700 has three seed/spacer retainer rings 701, 702, 703, as shown in FIG. 3A. A vacuum activated seed acceptance funnel 403 formed at an upper end of needle receptacle 207 extends through loading platform 700.

Figure 3B:
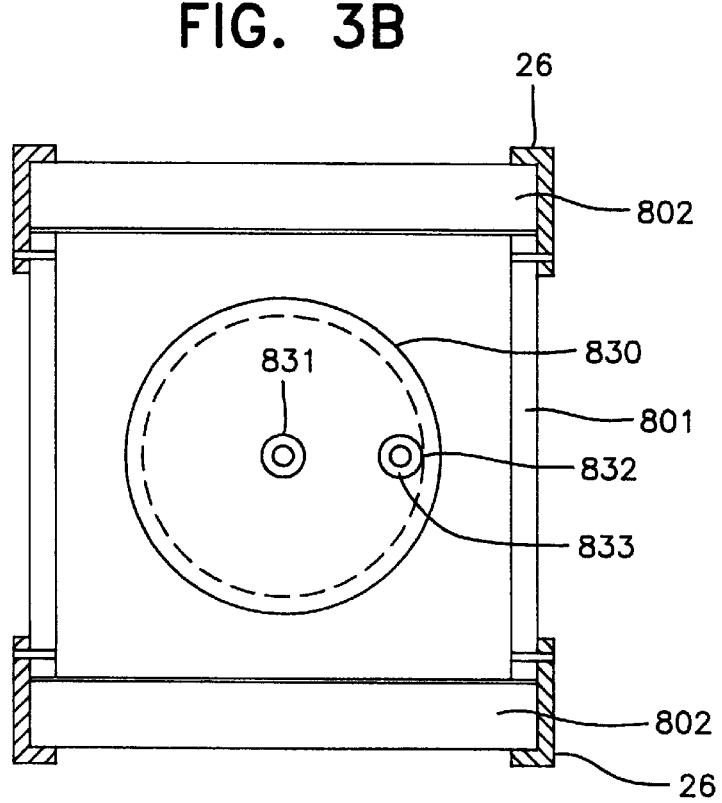
FIG. 3B is a plan view of the shield located on top of the loading platform.

A mini-dome shield 800 consisting of an inverted U-shaped metal dome 801, having front and back lead glass plates 802 clamped by bracket 26 to the other two metal walls and a top access plate 830 (FIG. 3B), is placed onto the loading platform 700 with its open side down. In an alternate embodiment, all four walls can be lead glass plates. Alternatively, the shield 800 may be made of a section of a lead glass cylinder.

The top access plate 830 of the dome shield 800 has a central opening 831 for receipt of a vacuum pickup probe 401. A side orifice 832 of the plate 830 has a removable plug 833 for pouring radioactive seeds onto the platform 700.

Seed spacers 301 are poured onto the loading platform 700 prior to placing the mini-dome shield 800 enclosure on loading platform 700 for radioactive seed loading as shown in FIG. 2. To further eliminate and/or reduce radiation exposure during transfer of seeds from a glass vial 303, contained in a lead shielded receiving bottle 304, to the loading platform, a funnel 302 and spout 305 are used as shown in FIG. 3.

The funnel 302 leads to a retainer ring 703. Spout 305 screws onto glass vial 303 and is oriented with respect to funnel 302 to permit the introduction of seeds directly into the seed/spacer retainer ring 703 on the loading platform 700 through the orifice 832 in the top access plate 830 of the mini-dome shield 800. The shield 800 is omitted from FIG. 3 for clarity. When another activity seed group retaining ring 702 (FIG. 3A) is required, the same funnel 302 and spout 303 can also be used.

4) Assuring and simplifying seed loading with a vacuum pickup probe and vacuum induced seed flow.

The vacuum pickup probe 401 is placed through the central opening 831 of the access plate 830 to manipulate seeds and spacers into the vacuum induced needle 10 (FIG. 2) through the acceptance funnel 403. Probe 401 is under a vacuum force which draws air in the direction of arrow 22. Finger releasing plunger 402 is a spring biased plunger which moves in and out of the vacuum stream through probe 401. When plunger 402 is moved into the path of the vacuum stream, the vacuum is prevented from being exerted onto probe 401. Accordingly, when plunger 402 is in its normally open position, probe 401 can pick up seeds 12 or spacers 301. The probe 401 is then located above funnel 403.

Plunger 402 is then depressed to cut off the vacuum force. Seeds and spacers drop under gravity into the acceptance funnel 403, needle tip 105 and into the needle 10 proper (FIG. 2).

In the event of vacuum failure, access plate 830 may be removed and forceps may be used to manipulate seeds and spacers into needle 10 by dropping seeds and spacers into funnel 403 by a gravity force.

Using the probe 401, retainer rings 701, 702, 703 can be pivoted about retainer ring pins 30 to turn their openings away from funnel 403. Seeds and spacers can thereby be prevented from accidently being sucked into funnel 403.

Seeds and spacers are loaded in an alternating fashion until the desired number and sequence for the particular needle 10 is achieved (e.g., 5 seeds and 4 spacers with seeds leading and ending). The loaded needle can now be disengaged from the needle receptacle 207 under the loading platform 700 by unscrewing set screw 14. Slip shield body 101 serves as a barrier to the seed bearing portion of the needle during loading, storage and transportation prior to removal for patient insertion during seed implantation. With the needle tip 105 still facing up, bone wax 404 is applied to seal the needle tip 105, and the slip shield body 101 is re-capped by screwing on end cap 206 to protect the needle tip 105. Cap 206 includes TEFLON plug 28 to protect needle tip 105. Plug 28 can also be used to set a proper needle tip protrusion from shield body 101 for docking with needle receptacle 207. With the needle tip then inverted to point down, to hold the seeds and spacers in the needle, the vacuum extension probe 201 is removed and a needle stylet 103 is inserted from above, as shown in FIG. 1, into the needle 10.

Figure 4:
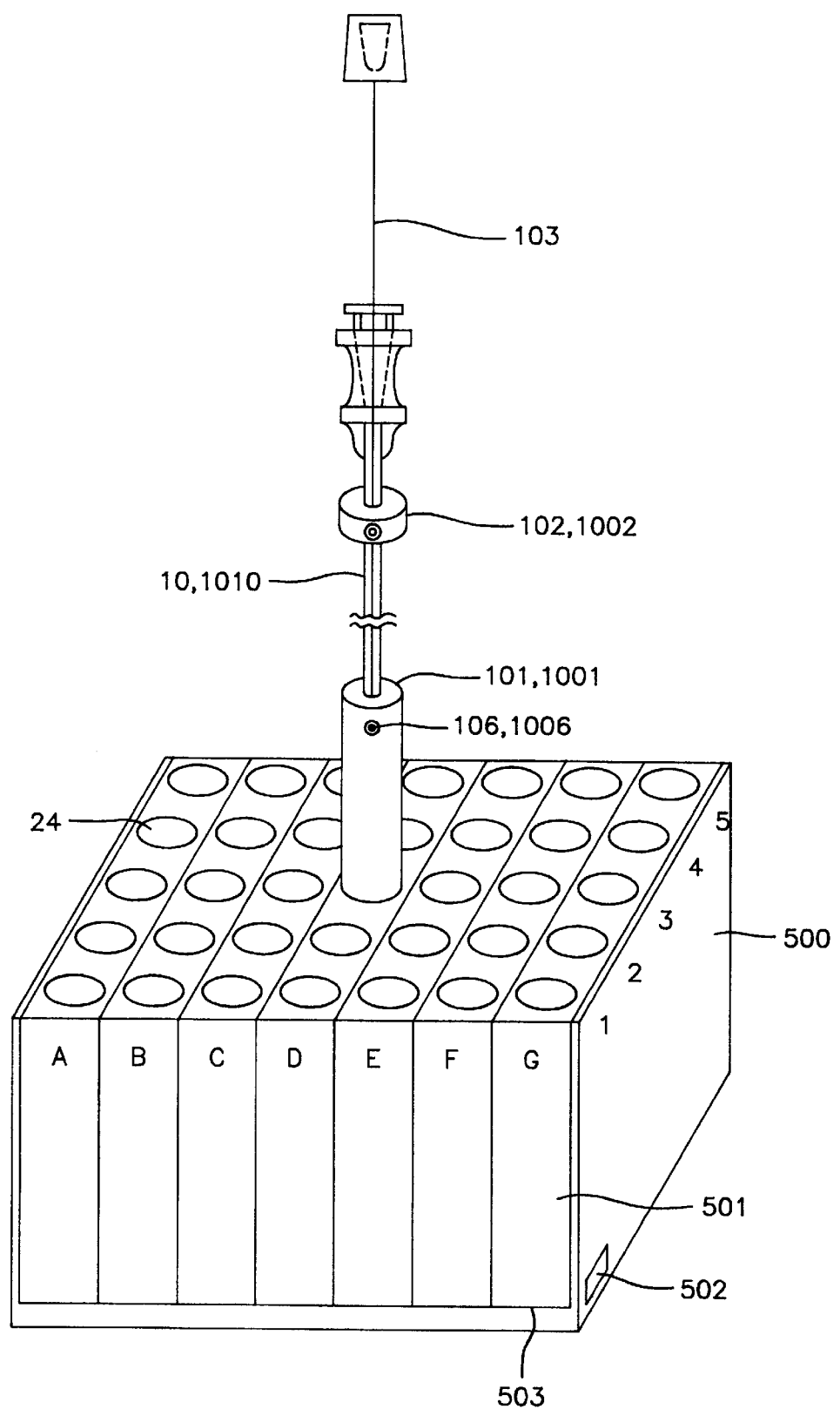
FIG. 4 is a perspective view of a needle slip shield holder box with only one assembled implant needle and slip shield shown, it being understood that a plurality of assembled implant needles and slip shields may be located in the needle holder box.

The stylet extension length is such that from the needle end, for example, with 5 seeds and 4 spacers, the length would be about 4.5 cm for standard I-125 seeds plus an additional 0.3 cm for bone wax, or approximately 4.7–4.8 cm. The needle locking collar screw 102 is then tightened to hold the stylet 103 by either a clamping force exerted through the needle 10 or by passage into an opening in a side of the needle 10 to engage the stylet 103. The stylet 103 is now also locked in the correct position. The needle with slip shield body 101 can now be placed into an individual opening 24 of needle holder box 500 as shown in FIG. 4. The above steps are repeated for each additional loaded needle with slip shield body 101 until all desired needles are loaded in tubes 24 according to plan.

5) Radiation slip shield needle holder.

A protective radiation slip shield needle holder box 500 is constructed for easy identification and access of implant needles as shown in FIG. 4. Needles with individual slip shield bodies 101 are assigned topologically into an array of retreatable columns 501 corresponding to a specified template needle assignment. Corresponding to the template needle assignment, each column 501 can be removed directly or rotated upon elevation about a hinge 502 and rest on the lip 503 of the three-sided box 500. Every seed-bearing needle is now ready and safe to be transported to the operating room for prostatic transperineal seed implantation.

An alternate embodiment of the present invention will be explained with reference to FIGS. 5A through 15.

Figure 5A:
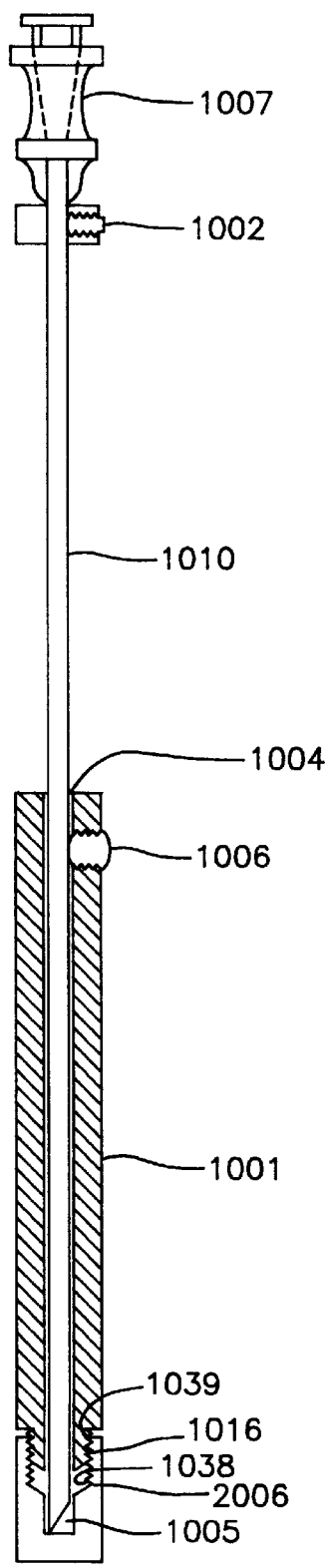
FIG. 5A is a partial sectional view of an assembled implant needle located within a needle slip shield body having a capped end.

FIG. 5A is a partial sectional view of an assembled implant needle located within a needle slip shield body with a capped end. The implant needle is locked in position with the needle tip resting on a cap.

Figure 5B:
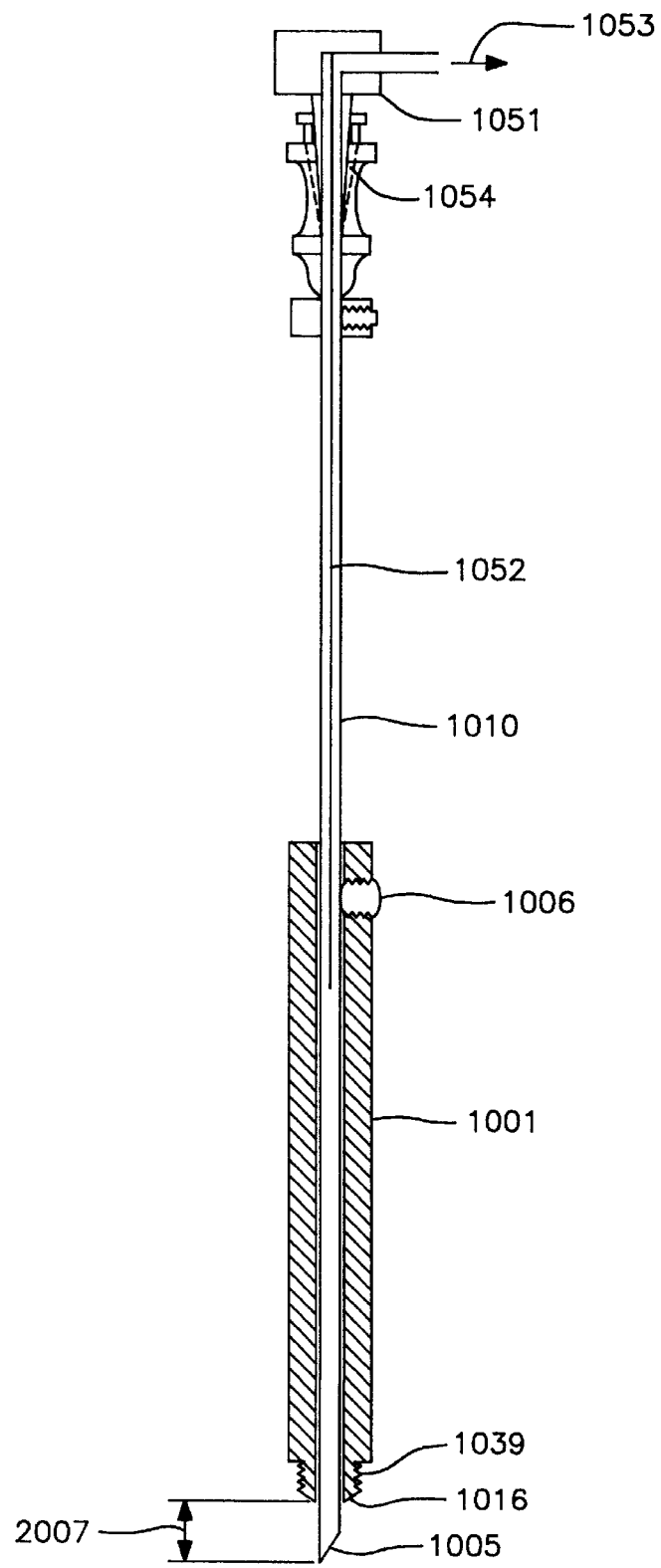
FIG. 5B is a partial sectional view of an implant needle located within a slip shield body and having a vacuum probe with a restricting pin located within the needle hub of the implant needle.

FIG. 5B is a sectional view of the receiving vacuum probe with a long restricting pin inserted into the needle hub in place of the needle stylet. The distal end of the needle tip protrudes from the slip shield tip in the locked position. The protrusion depth of the needle tip is critical to assure good vacuum flow and minimize vacuum losses starting from the bottom of the glass tube via the needle tip and into the implant needle. The receiving probe is tapered to fit snugly to the needle hub so that a vacuum seal is achieved. To further minimize vacuum loss, the slip shield tip is shaped to concavely match the docking convex funnel entrance, of the glass window tube shown in FIG. 8.

Figure 6:
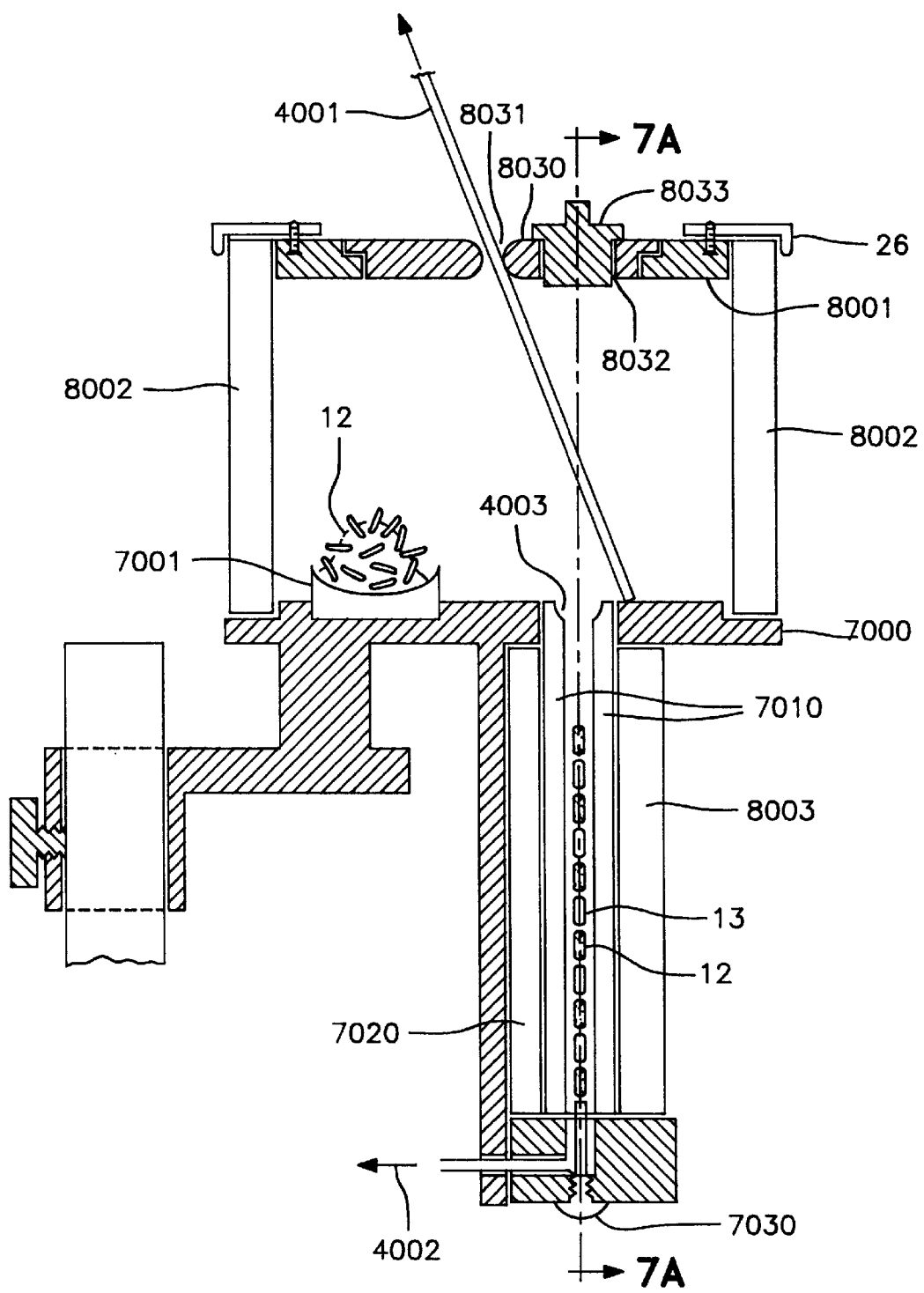
FIG. 6 is a side sectional view of the domed enclosure slidably mounted on a support rod and having a receiving glass tube extending downwardly from a loading platform with a funnel portion of the glass tube being located in the upper surface of the loading platform.

FIG. 6 is a sectional side view of the apparatus showing the first step of the two step loading procedure. In the first step, a predetermined sequence of radioactive seeds and spacers are shown loaded into the visible glass tube behind a lead glass plate. The glass tube and lead glass plate are constructed as part of the loading platform under the shielded dome.

The vacuum source inlets to the lower end of the glass tube and to the pickup probe are commonly connected. They work conjointly to place seeds/spacers into the visible glass tube in the first step of the two step process. Vacuum to the inlet near the lower end of the glass tube where the stopping pin is located pulls seeds/spacers down simultaneously as the vacuum inlet to the pickup probe is used to manipulate seeds/spacers into the glass tube. The glass tube and lead glass under the platform provide visual verification that the seed/spacer sequence and the total number of both are correct as per a Pre-Plan prior to the second step of vacuum transfer in FIG. 8.

Figure 7A:
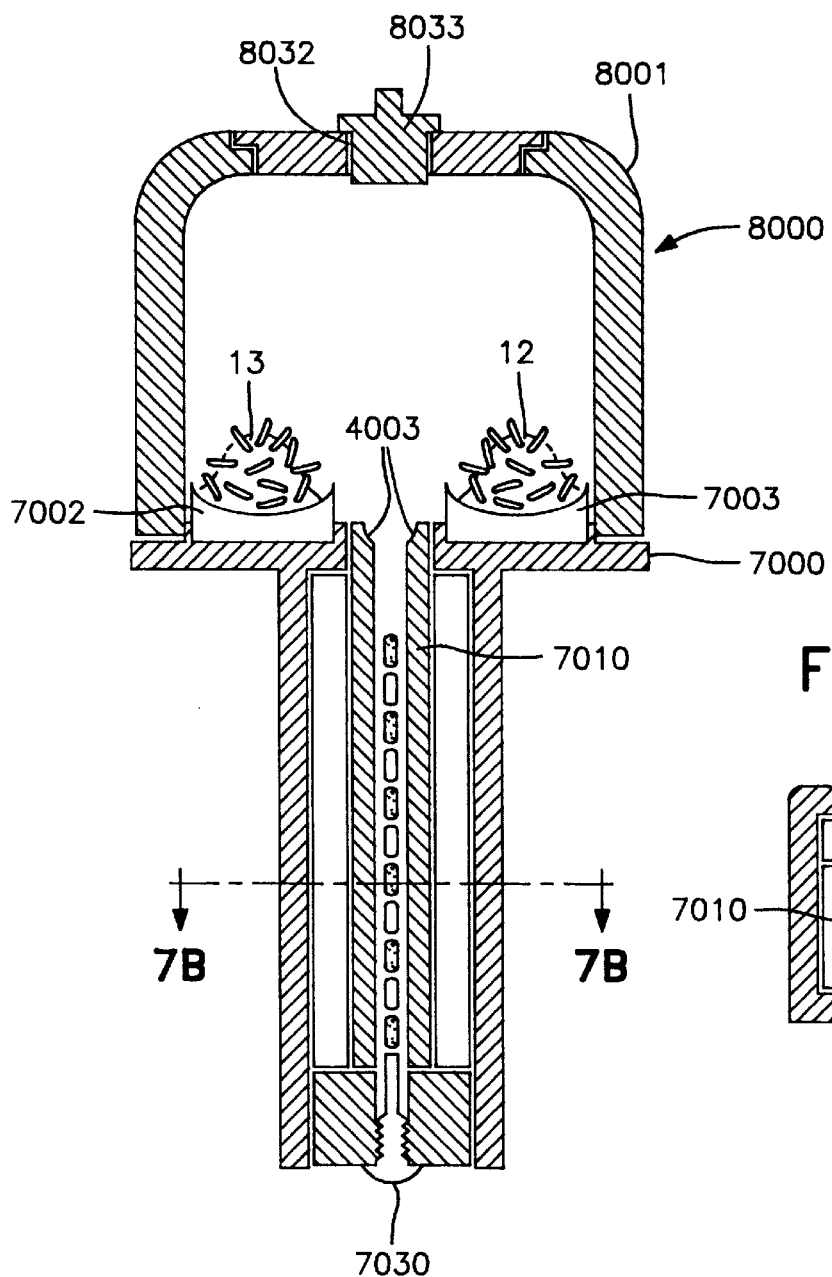
FIG. 7A is a sectional view taken along line 7A—7A of FIG. 6.
Figure 7B:
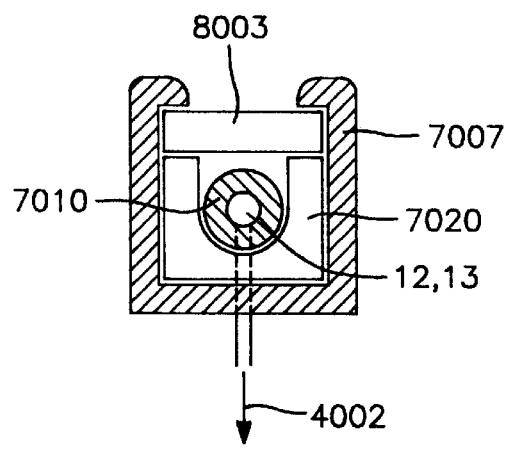
FIG. 7B is a cross-sectional view taken along line 7B—7B of FIG. 7A.

FIG. 7A is a front view of the apparatus. FIG. 7B is a cross sectional view of the glass tube and lead glass window for viewing the seed/spacer column. After visual verification, vacuum to the glass tube and the pickup probe is switched off. The funnel shape of the glass tube entrance is coupling matched to the curvature of the needle slip shield tip to reduce vacuum loss. The stopping pin at the base of the glass tube is intended to keep seeds/spacers in the viewing field.

The dome shown, for economic reasons, has only two, front and back, lead glass plates. A four-sided dome and a bell shaped lead glass dome are considered to incorporate the principles of the present invention.

Figure 8:
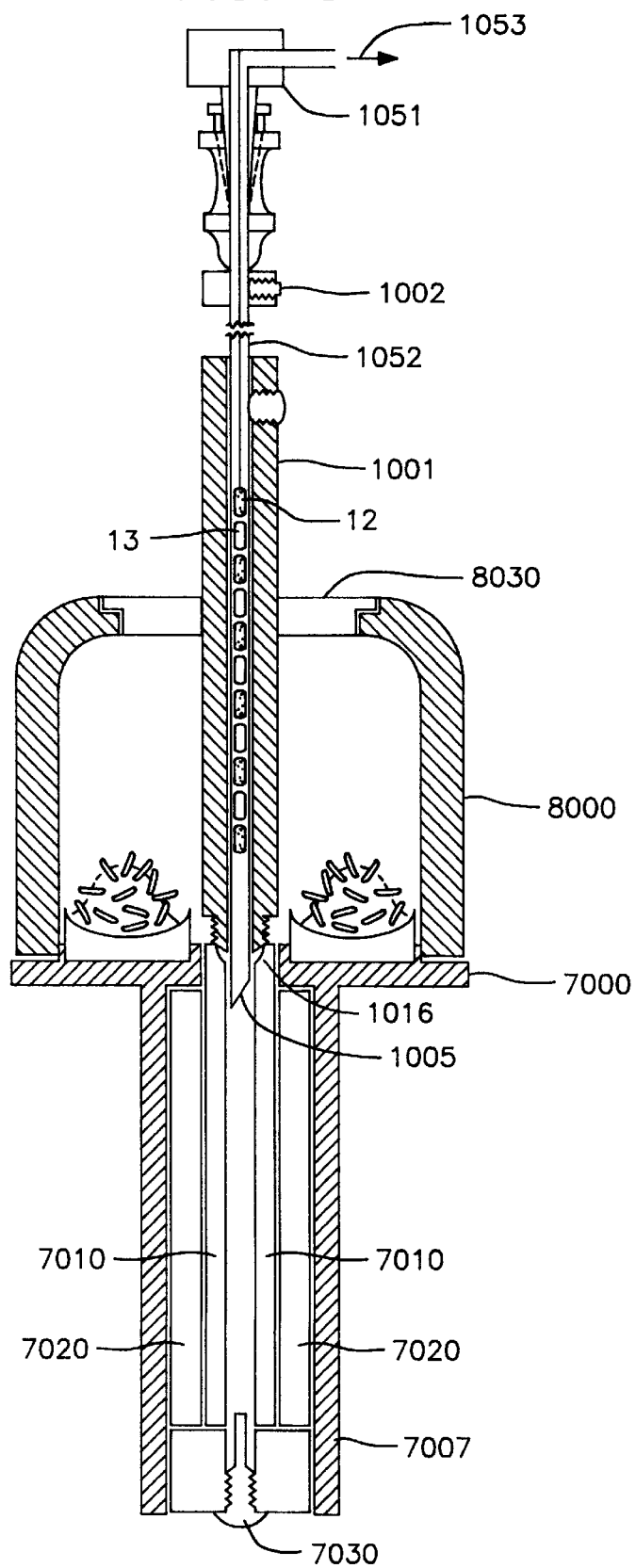
FIG. 8 is a sectional view showing a prepared implant needle evacuating a seed/spacer column from the glass tube.

FIG. 8 is a frontal sectional view of the apparatus showing a prepared implant needle receiving a seed/spacer column. The prepared implant needle is inside a slip shield with receiving probe inserted and slip shield cap removed.

In the second step of the two step loading process, the plug from the top access plate of the dome shield is removed and the prepared needle lowered with the needle tip pointing downward through the same opening until the needle tip meets and docks with the funnel entrance of the glass tube in the loading platform. With vacuum to the receiving probe activated, the seed/spacer column should be drawn up completely and at once into the shielded implant needle.

A manual bi-stable vacuum switch is provided for the two step loading procedure. Should some seeds or spacers remain in the window glass tube, the vacuum to the receiving probe is stopped using the switch or the vacuum hose to the receiving probe is pinched to interrupt the vacuum. The whole column of seeds/spacers will fall by gravity back into the visible glass tube and be drawn up again when the vacuum is again activated. This step is repeated if necessary until the whole column is completely transferred to the shielded needle.

Figure 9:
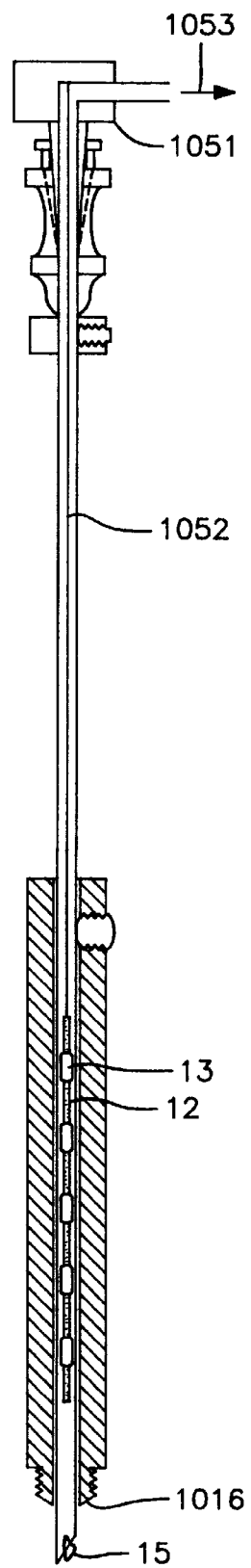
FIG. 9 is a partial sectional view of a loaded implant needle held within a slip shield body and sealed at its tip with bone wax.

In FIG. 9, while the receiving probe vacuum is active and after one has visually checked that the whole seed/spacer column has been completely transferred to the needle, the now loaded needle is removed from the domed enclosure. The needle tip is sealed with bone wax and the slip shield tip recapped before terminating vacuum to the receiving probe.

Figure 10:
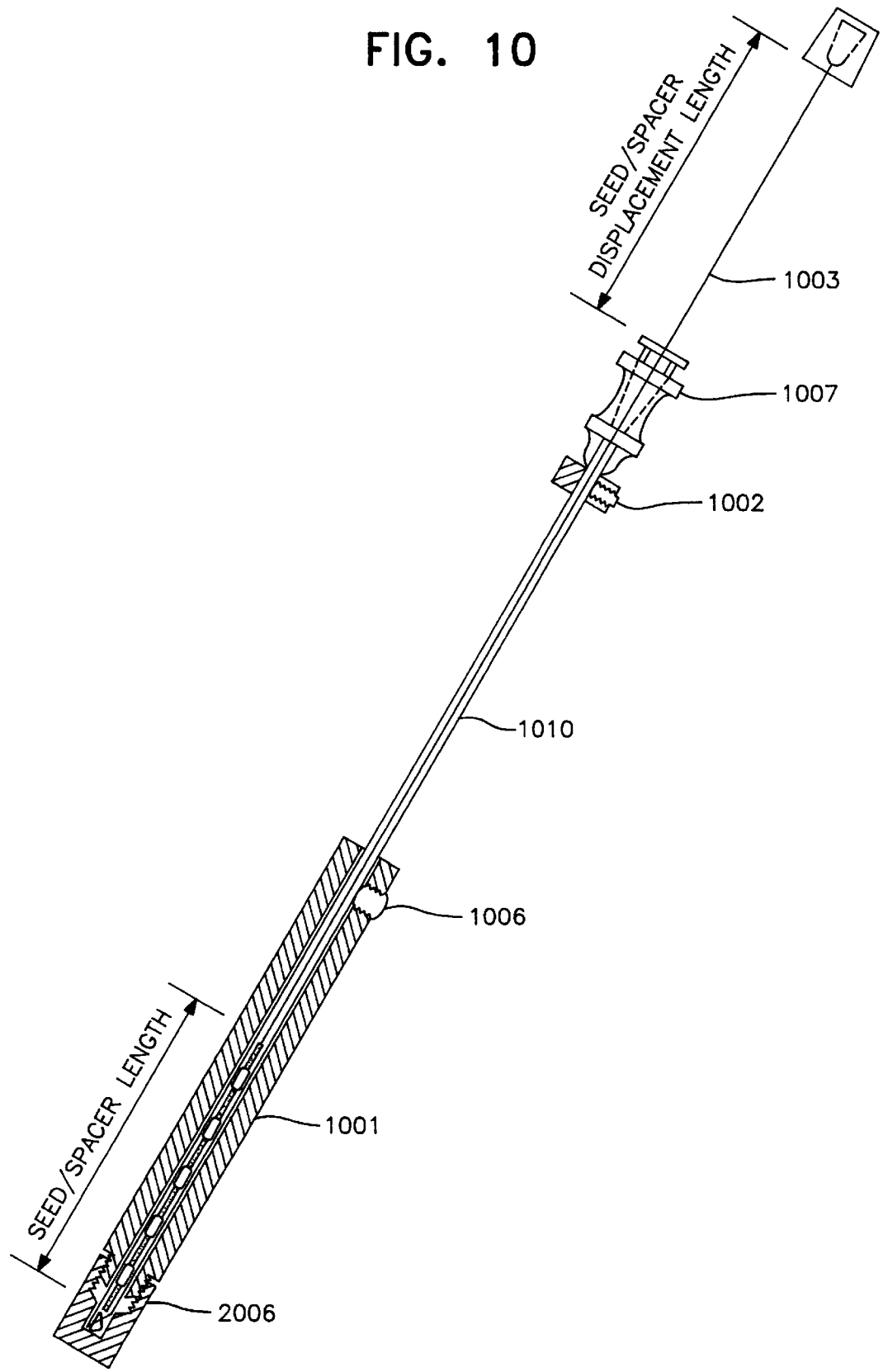
FIG. 10 is a partial sectional view of a loaded implant needle sealed with bone wax and capped and having a stylet inserted therein in place of the vacuum probe.

In FIG. 10, the receiving probe is removed from the shielded needle and replaced with the implant needle stylet to compare the displacement length of the stylet with respect to the total seeds and spacers loaded. The stylet now firmly rests against the top of the seed/spacer column. By tightening the locking collar, the stylet is locked to the implant needle thereby protecting the seed/spacer column inside from inadvertent movement. This specific assigned needle is now ready for the operating room seed implant procedure.

FIG. 4 is a perspective view of a needle slip shield holder box with one assembled implant seed bearing needle, with its slip shield, at location D-3. It is understood that a plurality of assembled implant needles and slip shields are required with a number of specific seeds/spacers for each assigned needle location (e.g. D-3) corresponding to the template assignment. The specific seed/spacer assignment is derived from a Pre-Plan based on a set of axial ultrasound scans superimposed on a 1 cm template grid commonly known as a volume study and in combination with known urological findings.

The box markings correspond to template hole markings where seed bearing implant needles will be inserted through corresponding holes of the template one at a time into the patient. The insertion depth of each implant needle into the patient is verified visually through a fiber optic cystoscopic procedure.

The various steps involved in the method of the present invention will now be explained with reference to the drawings. The steps are performed as follows:

1) Placement of a radiation slip shield body 1001 on individual needles prior to seed loading.

A needle locking collar 1002 is placed onto an empty implant needle 1010 as shown in FIG. 5A. In this Figure, the stylet has been removed. The needle 1010 is inserted into the opening 1004 of a protective needle slip shield body 1001. Needle tip 1005 is pointing downwardly, as shown in FIG. 5A, and extends past the slip shield tip 1016 to rest passively on the inside of the slip shield cap 2006.

Slip shield tip 1016 includes external threads 1039 and slip shield cap 2006 includes internal threads 1038. As the radially extending slip shield lock screw 1006 is tightened, it passes through the slip shield body 1001 and contacts the implant needle 1010, fixing the relative position between the needle 1010 and slip shield body 1001.

Although the needle slip shield body 1001 can be constructed more economically from a single material such as stainless steel, for more efficient radiation shielding, lead or other higher atomic number materials can also be used. Also, two concentric tubes may be used with lead fill material between the two tubes. This construction principle is demonstrated in U.S. Pat. No. 5,147,282, herein incorporated in its entirety by reference.

The slip shield cap 2006 protects and allows access to the needle tip 1005. The amount of internal threading of the cap 2006 onto the external threading of the tip 1016 sets the protrusion depth 2007, seen in FIG. 5B, of the needle from the slip shield tip 1016. This depth assures good vacuum flow later, during transfer of the seed/spacer column, as in FIG. 8, minimizing vacuum loss from the bottom of the glass tube 7010 via the needle tip 1005 into the implant needle 1010.

A vacuum receiving probe 1051 with a long seed restricting pin 1052 is inserted into the implant needle 1010 through the needle hub 1007 in the place that will later be occupied by the needle stylet 1003. With a vacuum force to both vacuum pickup probe 4001 and glass tuba vacuum inlet 4002 de-activated the implant needle 1001 is ready to received predetermined sequence of seeds/spacers.

2) introduction of seeds and spacers to the platform loading.

A loading platform 7000 has three seed/spacer holding cups 7001, 7002, and 7003 as shown in FIGS. 6 and 7A. A vacuum activated funnel entrance 4003, level with the upper surface of the loading platform 7000, forms the upper end of the glass tube 7010. The lower end of the glass tuba 7010 is partially blocked by stopping pin 7030 to allow for visual viewing and verification through lead glass window 8003 (FIG. 7B) while maintaining vacuum is flow through inlet 4002 for pulling seeds/spacers into glass tube 7010.

A domed shield enclosure 8000 consisting of an inverted U-shaped metal dome 8001, having front and back lead glass plates 8002 (FIG. 6) clamped by bracket 26 to the two metal walls 8001 and a circular top access plate 8030 (FIGS. 6 and 7A), is placed onto the loading platform 7000 with its open side down. In an alternative embodiment, all four wall& con be lead glass plates. Alternatively, the shield 8000 may be made of a section of a lead glass cylinder.

Figure 11:
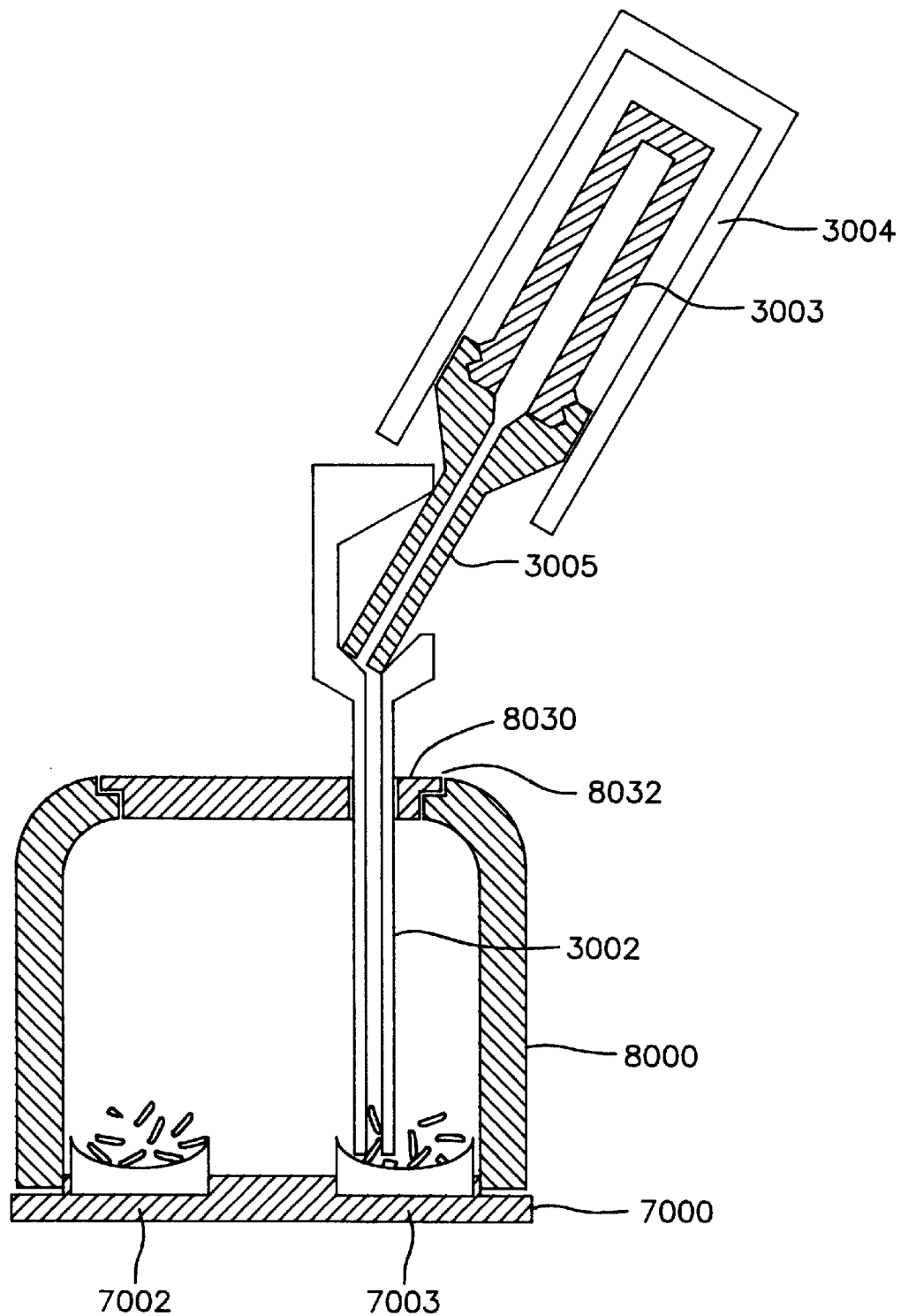
FIG. 11 is a sectional view of a specialized funnel and spout arrangement for loading radioactive seeds into a cup on the loading platform housed within the domed enclosure.

The top access plate 8030 of the domed shield 8000 has a central opening 8031 (FIG. 6) for receipt of a vacuum pickup probe 4001. A side orifice 8032 of the plate 8030 has a removable plug 8033 for pouring radioactive seeds onto the platform 7000 as shown in FIG. 11.

Spacers 13 are poured into one of the three cups 7002 (7001, 7003) on the loading platform 7000 prior to placing the domed shield 8000 enclosure on loading platform 7000 for later radioactive seed loading, as shown in FIG. 6. To further eliminate and/or reduce radiation exposure during transfer of seeds from glass vial 3003 (FIG. 11), contained in a lead shielded receiving bottle 3004, to the loading platform, a funnel 3002 and spout 3005 are used as shown in FIG. 11.

The funnel 3002 leads to an empty cup 7001 (or 7003). Spout 3005 screws onto glass vial 3003 and is oriented with respect to funnel 3002 to permit the introduction Of seeds directly into an empty cup 7001 (or 7003) on the loading platform 7000 through the side orifice 8032 in the top access plate 8030 of the domed shield 8000. If other radioactive seed activity is required, the remaining empty cup 7003 (or 7001) may be used with the same funnel 3002 and spout 3005.

3) Assuring and simplifying seed loading with a vacuum pickup probe 4001 and vacuum induced glass tube 7010 forming a seed/spacer column for visual verification through lead glass plate 3002 prior to needle loading.

The vacuum pickup probe 4001 is placed through the central opening 8031 of the access plate 8030 to manipulate seeds and spacers through the funnel 4003 of glass tube 7010 by a vacuum induced through vacuum inlet 4002 to form a seed/spacer column behind a lead glass viewing window 3002 (FIG. 6). The vacuum to both hollow pickup probe 4001 and glass tube inlet 4002 is created from a single vacuum source. The pickup probe 4001 and inlet 4002 are connected at two branches of a T-split from the vacuum source. They work together to place seeds/spacers into the visible glass tube 7010.

Pickup probe 4001 uses a finger releasing action over an opening in the side of the probe 4001 leading to its hollow interior through which vacuum is applied to control its vacuum activity. When the vacuum control opening on probe 4001 is covered by a finger, probe 4001 can pick up seeds 12 or spacers 13. A glass tube 7010 having lead glass plate 8003 in front of it acting as a shield is attached beneath the loading platform 7000 of the shielded domed enclosure 8000 with entrance to the glass tube through funnel 4003 in the platform 7010. A stopping pin 7030 at the base of glass tube 7010 keeps the seed/spacer column in full view through plate 8003 while maintaining vacuum flow for pulling seeds/spacers from funnel 4003 into glass tube 7010 while it is being loaded.

The probe 4001 is located above funnel 4003 in the loading platform 7000. By uncovering the vacuum control opening by removal of a finger, the vacuum force to probe 4001 is shut off allowing seeds 12 or spacers 13 previously held in place on the probe 4001 by the applied vacuum force to drop through funnel 4003 into glass tube 7010 by gravity and with vacuum assistance from vacuum inlet 4002 which maintains continuous vacuum in a downwardly direction through glass tube 7010 during pickup and dropping of seeds 12 or spacers 13. Seeds 12 and spacers 13 are loaded through funnel 4003 into glass tube 7010 in an alternating fashion until the desired number and sequence, defined by the user according to a Pre-Plan for each particular needle 1010, is achieved (e.g., 5 seeds and 4 spacers with seeds leading and ending).

A white TEFLON backing 7020 placed behind glass tube 7010 provides a contrasting visual background for viewing/verifying the seed/spacer column sequence and the lead glass plate 8003 provides a radiation shielded window in front for safely viewing the seed/spacer column in glass tube 7010. The number and sequence of seeds and spacers is visually verified and ready for transfer to implant needle 1010 within slip shield body 1001.

4) Vacuum transfer of seed/spacer column from glass tube 7010 into a prepared implant needle 1010 inside a slip shield 1001 with receiving probe 1051 inserted and slip shield cap 2006 removed as shown in FIG. 5B.

Plug 8033 is removed from opening 8032 of access plate 8030 of the domed shield enclosure 8000 as shown in FIG. 5B and FIG. 8. The prepared needle with needle tip 1005 is lowered, pointing downward through the opening 8032, until the needle tip 1005 extends into the funnel entrance 4003 of the glass tube 7010 in the loading platform 7000. The lowermost surface of slip shield tip 1016 is complementarily shaped as a convex protrusion to matingly fit into the concave curvature of the uppermost edge of glass tube 7010 which forms funnel 4003.

This apparatus provides a manual bi-stable vacuum switch 5000 as shown in FIG. 12 with one tube communicating by plastic tubing with the inlet 1053 for receiving probe 1051 as in FIG. 8 and the other tube splitting and communicating with the pickup probe 4001 and the glass tube inlet 4002 as in FIGS. 12–14. With only vacuum inlet 1053 to the receiving probe 1051 activated, the seed/spacer column is drawn up completely from the glass tube 7010 into the shielded implant needle.

Should some seeds or spacers remain in the window glass tube 7010, the vacuum to the receiving probe 1051 is stopped by using the switch 5000 or by pinching the vacuum hose communicating with the receiving probe 1051. The whole column of seeds/spacers will then, upon interruption of the vacuum to vacuum inlet 1053, fall back by gravity into the glass tube 7010. Once the vacuum is re-initiated, the seeds/spacers will be drawn up again into implant needle 1010. These steps are repeated if necessary until the whole column is completely transferred to the shielded needle 1010 as in FIG. 8.

With the vacuum inlet 1053 to the receiving probe 1051 still active, and after having visually checked that the glass tube 7010 is completely empty and therefore the whole seed/spacer column has been completely transferred to the needle, the now loaded needle within its slip shield body is removed from the domed enclosure 8000. The needle tip 1005 is sealed with bone wax 15 as in FIG. 9 and cap 2006 is replaced over the slip shield tip 1016 before vacuum to inlet 1053 of the receiving probe 1051 is terminated.

Receiving probe 1051 is removed from the loaded needle and replaced with the implant needle stylet 1003. The displacement length of the stylet is compared with respect to the total seeds and spacers loaded to confirm proper loading. The stylet 1003 now firmly rests against the top of the seed/spacer column. By tightening the locking collar 1002, the stylet 1003 is locked to the implant needle 1010 thereby protecting the seed/spacer column inside from inadvertent movement. This specific assigned needle is now ready for the operating room seed implant procedure.

The switch 5000 is pivotally mounted on platform 5002 by pivot pin 5004 being slidably mounted in opening 5006 in the platform body. The platform body includes three openings labeled as A, B, C.

Opening A, as shown in FIG. 14, extends partially through the platform 5002 to act as a closed port. Opening B is in communication with a tube 5008 which is connected to a vacuum source or pump as indicated by arrow 5010, by plastic tubing. Opening C extends through the platform 5002 so as to provide ambient air therethrough.

Vacuum switch 5000 is positionable to two positions so as to change the communication of the vacuum source with various components of the present invention. Switch 5000 includes two tubes.

As shown in FIG. 12, short tube ("S") 5012, in the position shown in FIGS. 12 and 13, is in communication through tube 5008 with vacuum pump 5010. In this position, a vacuum force is applied through tube 5012 which is in communication, by plastic tubing, with both glass tube inlet 4002 as wall as a vacuum inlet to pick up probe 4001. With the switch 5000 in this position, as explained in FIG. 15, the receiving probe 1053 in communication with long tube ("L") 8014, communicates with a closed port.

Figure 15:
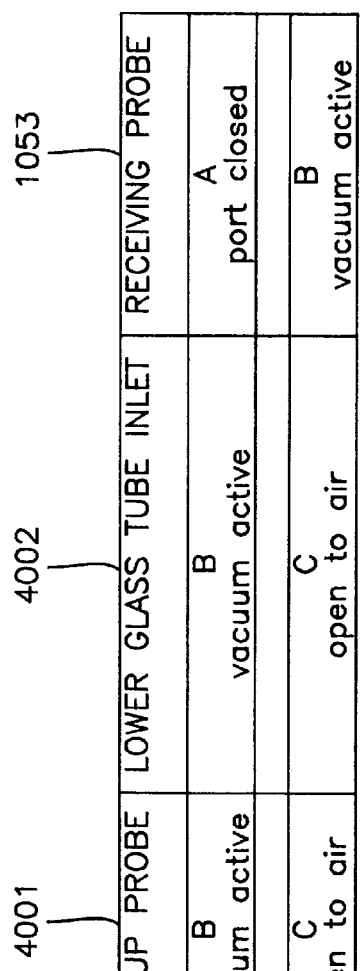
FIG. 15 is a vacuum activity flow table for control of evacuated air in the two steps of the present invention.

When the switch 5000 is picked up and rotated about pin 5004, so that tube 5012 is located in opening C and tube 5014 is located in opening a, as explained in the stop two position of FIG. 15, the pick up probe 4001 and the lower glass tube inlet 4002 are opened to the ambient air by opening C. However, in this position, receiving probe 1053 is provided with communication to the vacuum source 5010 so as to pick up a seed/spacer column as shown in FIG. 8.

5) Radiation slip shield needle holder.

A protective radiation slip shield needle holder box 500 is constructed for easy identification and access of implant needles as shown in FIG. 4. Needles within individual slip shield bodies 1001 are assigned topologically during loading into an array of retreatable columns 501 corresponding to a specified template needle assignment. Each column 501 ran be removed or rotated about a hinge 502 and pivot to rest on the lip 503 of the three-aided box 500. Every seed-bearing needle is thereby organized and safe to be transported to the operating room for prostatic transperineal seed implantation.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. An apparatus for handling radioactive seeds and spacers, said apparatus comprising:

a loading platform for containing radioactive seeds, an enclosed radiation shield mounted on said loading platform to define a handling space for the radioactive seeds and spacers, a tube having a funnel entrance, said funnel entrance being located in said loading platform for accepting seeds/spacers to form a seed/spacer column in said tube, said tube being made of glass for visual verification of proper seed and spacer sequences, an end of the tube opposite to the funnel entrance including a vacuum inlet, and a probe extending into said handling space, said probe being connected to a controllable vacuum source for exerting a vacuum force from said probe on radioactive seeds and spacers located in said handling space so that said probe may pick up and release radioactive seeds or spacers into the tube.

2. An apparatus for handling radioactive seeds and spacers as claimed in claim 1, wherein said radiation shield includes lead glass.

3. An apparatus for handling radioactive seeds and spacers an claimed in claim 1, wherein said radiation shield includes an opening for passage therethrough of said probe.

4. An apparatus for handling radioactive seeds and spacers as claimed in claim 1, wherein said glass tube funnel entrance is shaped in a convex curvature matching a concave shaped surface of a slip shield tip.

5. An apparatus for handling radioactive seeds and spacers as claimed in claim 1, wherein the end of the glass tube opposite to the funnel entrance includes an adjustable stopping pin for adjusting a height of a seed/spacer column while maintaining vacuum flow therethrough.

6. An assembly for handling radioactive seeds and spacers as claimed in claim 1, wherein said vacuum inlet of the tube and a vacuum inlet to the probe are simultaneously connected to the vacuum source.

7. An apparatus for handling and loading radioactive seeds into needles, said apparatus comprising:

a loading platform for containing radioactive seeds and spacers, a shield mounted on said loading platform to define an enclosed handling space for the radioactive seeds and spacers, a tube having a funnel entrance, said funnel entrance being located in said loading platform for accepting seeds/spacers to form a seed/spacer column in said tube, a probe extending into said handling space, said probe being connected to a controllable vacuum source for exerting a vacuum force from said probe on radioactive seeds and spacers located in said handling space so that said probe may pick up and release radioactive seeds or spacers in the tube, a receiving probe having a restricting pin and a vacuum inlet for connection to a vacuum source, an empty needle for receiving the vacuum receiving probe to exert a vacuum force from a hub end of the needle, and a slip shield having a cap at one end for housing a distal part of the needle and then introducing the slip shield into the handling space after removing the cap to pick up a seed/spacer column resting in the tube.

8. An assembly for handling and loading radioactive seeds as claimed in claim 7, wherein the slip shield surrounds the distal part of the needle including a needle tip.

9. An assembly for handling and loading radioactive seeds as claimed in claim 7, wherein the slip shield has a slip shield tip with external threads.

10. An assembly for handling and loading radioactive seeds as claimed in claim 9, wherein the slip shield tip has a convex shape matched to a concave curvature of the tube funnel entrance.

11. An assembly for handling and loading radioactive seeds as claimed in claim 7, wherein the slip shield has a slip shield tip with external threads matched with internal threads of the slip shield cap.

12. An assembly for handling and locating radioactive seeds as claimed in claim 11, wherein the slip shield cap sets a needle tip protrusion depth from the slip shield tip, the needle tip protrusion depth is used in picking up a seed/spacer column from the tube and into the needle.

13. An assembly for handling and loading radioactive seeds as claimed in claim 7, wherein the receiving probe includes a tapered coupling surface for fitting with an interior surface of the needle hub to provide a vacuum seal.

14. An assembly for handling and loading radioactive seeds as claimed in claim 7, wherein the receiving probe includes the restricting pin so as to prevent a seed/spacer column from moving past the slip shield when radiation protection is needed, thereby maintaining the seed/spacer column at the distal end of the needle.

15. An assembly for handling and loading radioactive seeds as claimed in claim 7, wherein said shield includes an opening for passage of said probe into said handling space.

16. An assembly for handling and loading radioactive seeds an claimed in claim 15, wherein said shield includes a circular access plate containing said opening and also includes a side orifice containing a plug.

17. An assembly for handling and loading radioactive seeds as claimed in claim 7, wherein said slip shield cap allows access to the needle tip for sealing the needle tip with bone wax when a seed/spacer column is in the needle.

18. An assembly for handling and loading radioactive seeds as claimed in claim 7, wherein said tube is made of glass to visually verify a proper sequence of seeds and spacers.

19. An apparatus for handling radioactive seeds and spacers, said apparatus comprising:

a loading platform for containing radioactive seeds and spacers, an enclosed radiation dome shield extending from said loading platform to define a handling and loading space for the radioactive seeds and spacers, and a tube having a funnel entrance, said funnel entrance being located in said loading platform for accepting seeds/spacers to form a seed/spacer column in said tube, said tube being transparent and shielded by a transparent radiation tube shield for visual verification of a proper seed and spacer sequence, said radiation dome shield being an at least partially transparent shield for viewing said loading platform and said funnel entrance of said tube through said radiation dome shield and visually verifying proper seed and spacer loading sequences into said tube through maid radiation dome shield and visually verifying said proper seed and spacer sequence in said tube through said transparent radiation tube shield from at least one side of the tube.

20. An apparatus for handling radioactive seeds and spacers as claimed in claim 19, wherein said radiation dome shield includes an opening for passage therethrough of a probe.

21. An apparatus for handling radioactive seeds and spacers as claimed in claim 19, wherein said tube funnel entrance is shaped in a convex curvature matching a concave shaped surface of a slip shield tip.

22. An apparatus for handling radioactive seeds and spacers as claimed in claim 19, wherein an end of the tube opposite to the funnel entrance includes a vacuum inlet.

23. An apparatus for handling radioactive seeds and spacers as claimed in claim 22, wherein the end of the tube opposite to the funnel entrance includes an adjustable stopping pin for adjusting a height of a seed/spacer column while maintaining vacuum flow therethrough.

24. An assembly for handling radioactive seeds and spacers as claimed in claim 22, wherein said vacuum inlet of the tube is adapted to be connected to a vacuum source.

* * * * *